United States Patent
Rigie et al.

(10) Patent No.: US 9,437,016 B2
(45) Date of Patent: Sep. 6, 2016

(54) IMAGE DOMAIN PANSHARPENING METHOD AND SYSTEM FOR SPECTRAL CT WITH LARGE PIXEL ENERGY DISCRIMINATING DETECTORS

(71) Applicants: THE UNIVERSITY OF CHICAGO, Chicago, IL (US); TOSHIBA MEDICAL SYSTEMS CORPORATION, Otawara-Shi, Tochigi-Ken (JP)

(72) Inventors: David Rigie, Chicago, IL (US); Patrick La Riviere, Chicago, IL (US); Adam Petschke, Lake Bluff, IL (US)

(73) Assignees: Toshiba Medical Systems Corporation, Otawara-shi (JP); The University of Chicago, Chicago, IL (US)

( * ) Notice: Subject to any disclaimer, the term of this patent is extended or adjusted under 35 U.S.C. 154(b) by 165 days.

(21) Appl. No.: 13/960,819

(22) Filed: Aug. 7, 2013

(65) Prior Publication Data
US 2015/0043795 A1 Feb. 12, 2015

(51) Int. Cl.
*A61B 6/00* (2006.01)
*G06T 11/00* (2006.01)
*G06T 5/00* (2006.01)
*G06T 3/40* (2006.01)
*G06T 5/50* (2006.01)

(52) U.S. Cl.
CPC .......... *G06T 11/008* (2013.01); *A61B 6/4241* (2013.01); *G06T 3/4061* (2013.01); *G06T 5/003* (2013.01); *G06T 5/50* (2013.01); *G06T 2207/10081* (2013.01); *G06T 2207/10108* (2013.01); *G06T 2210/41* (2013.01)

(58) Field of Classification Search
CPC .............. G06T 2207/10036; G06T 11/005; G06K 9/0063; A61B 6/4241; A61B 6/032; A61B 6/482
See application file for complete search history.

(56) References Cited

U.S. PATENT DOCUMENTS 5,949,914 A * 9/1999 Yuen ............................ 382/254
8,487,996 B2 * 7/2013 Mann et al. ................. 348/144
(Continued)

OTHER PUBLICATIONS

Mitchell, Image Sensors in chapter 2 of Image Fusion, 2010 [retrieved May 20, 2016], Springer Berlin Heidelberg,pp. 9-17. Retrieved from the Internet: http://link.springer.com/chapter/10.1007/978-3-642-11216-4_2.*
Edward W. Mowle and Cornelius J. Dennehy, The Landsat-6 Satellite: An Overview, Telesystems Conference, 1991. Proceedings, Mar. 26-27, 1991, pp. 277-282, vol. 1, IEEE, Atlanta, GA.
(Continued)

*Primary Examiner* — Matthew Bella
*Assistant Examiner* — Dennis Rosario
(74) *Attorney, Agent, or Firm* — Ken I. Yoshida

(57) ABSTRACT

A hybrid CT dataset is obtained from a combination of a integrating detector and a photon-counting detector. The hybrid CT dataset contains low-resolution photon-counting data and high-resolution integrating data. High-resolution panchromatic images are generated from the high-resolution integrating data, and low-resolution spectral images are generated from the low-resolution photon-counting data. The high-resolution panchromatic images inherit the resolution properties of the integrating detector while the low-resolution spectral images inherit the spectral information of the photon-counting detector. Subsequently, the low resolution spectral images are pansharpened based upon at least one high resolution panchromatic image that lacks spectral information according to a pansharpening algorithm.

13 Claims, 8 Drawing Sheets

(56) References Cited

U.S. PATENT DOCUMENTS

| | | | |
|---|---|---|---|
| 8,717,361 B2* | 5/2014 | Sasakawa et al. | 345/427 |
| 8,772,730 B2* | 7/2014 | Han | G01T 1/247 250/363.01 |
| 2007/0076842 A1* | 4/2007 | Tkaczyk | A61B 6/032 378/5 |
| 2013/0284939 A1* | 10/2013 | DeMan | A61B 6/032 250/393 |
| 2015/0036902 A1* | 2/2015 | Zamyatin et al. | 382/131 |
| 2015/0043796 A1* | 2/2015 | Rigie et al. | 382/131 |

OTHER PUBLICATIONS

Coloma Ballester, et al., A Variational Model for P+XS Image Fusion, International Journal of Computer Vision 69, Apr. 2006, pp. 43-58, No. 1, Spring Science+Business Media, LLC., The Netherlands.

Zeming Zhou, et al., Pan-sharpening: a Fast Variational Fusion Approach, Science China Information Sciences, Mar. 2012, pp. 615-625, vol. 55 No. 3, Science China Press and Springer-Verlag Berlin Heidelberg.

* cited by examiner

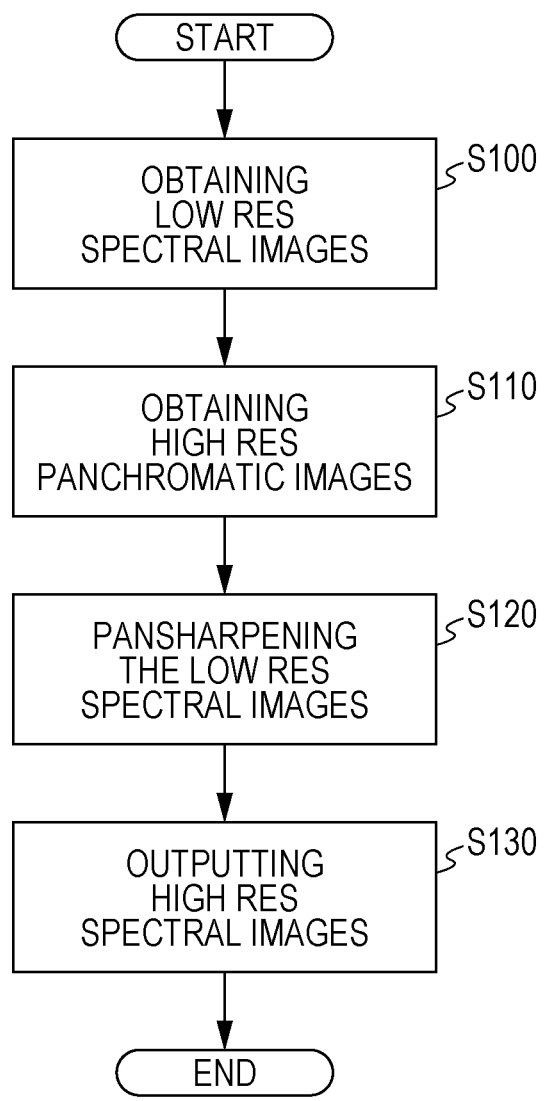

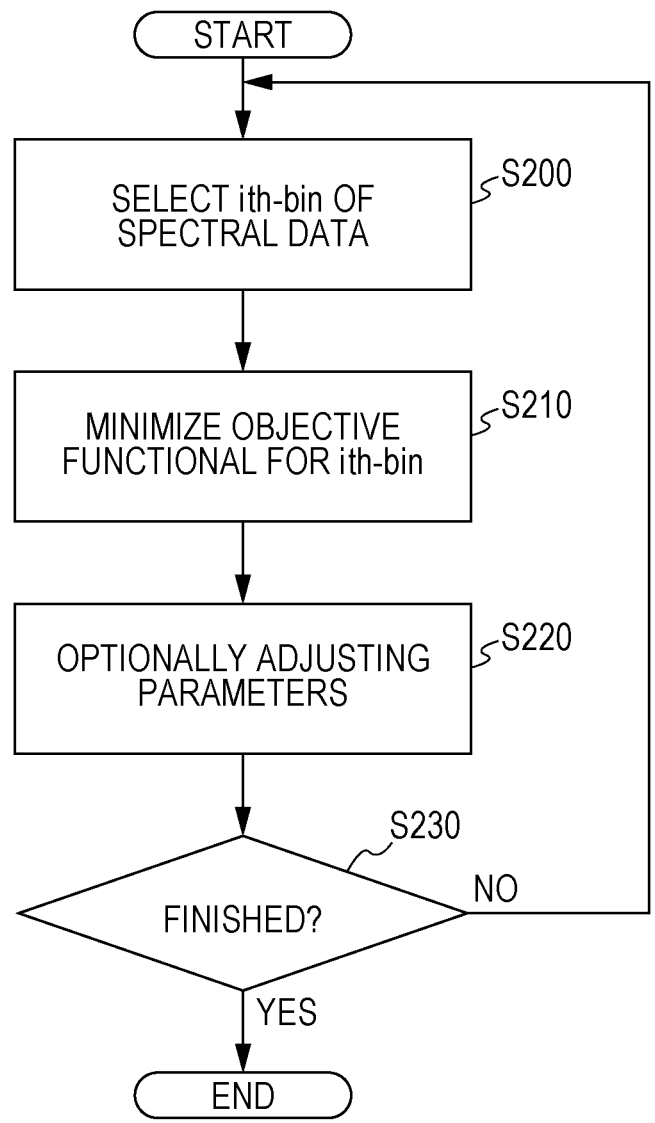

GROUND TRUTH – 512×512

INPUT IMAGE – 128×128

PAN-SHARPENED IMAGE

IMAGE DOMAIN PANSHARPENING METHOD AND SYSTEM FOR SPECTRAL CT WITH LARGE PIXEL ENERGY DISCRIMINATING DETECTORS

FIELD OF THE INVENTION

The current invention is generally related to computer tomography (CT) image processing, and more particularly related to pansharpening of CT low-resolution spectral images using a high-resolution panchromatic (non-spectral) image.

BACKGROUND OF THE INVENTION

There is great desire to incorporate photon-counting detectors also known as energy discriminating X-ray detectors in computed tomography (CT). The photon-counting detectors have some potential to improve image quality, reduce dose and enable new clinical applications of CT. The photon-counting detectors acquire data including extra spectral information for providing material classification, improving quantitative imaging and reducing beam-hardening artifacts.

Despite the above advantages over widely used energy-integrating detectors, the photon-counting detectors have certain disadvantages. The photon-counting detectors are generally limited by the high costs and their count-rate. Furthermore, although the signal-to-noise ratio (SNR) in the photon-counting detectors is reduced at low flux levels for a small pixel size, the photon-counting detectors experience an increased level of inter-pixel interference due to the small pixel size. On the other hand, the photon-counting detectors such as CdTe/CdZnTe sensors have poor performance at high flux levels, and consequently the SNR deteriorates. For these reasons, the photon-counting detectors have not yet replaced the energy-integrating detectors currently utilized in clinical CT systems.

Because of the above described issues of the photon-counting detectors, a dual-tube CT system has been proposed to utilize a combination of photon-counting detectors and integrating detectors. In one exemplary dual-tube CT system, one source projects X-ray towards a photon-counting detector while the other source projects X-ray towards a conventional detector that is placed at a predetermined angle with respect to the photon-counting detector. In order to cope with the high flux rates used in the exemplary dual-tube CT system, the pixel-size of the photon-counting detector was made substantially small, but charge sharing and K-escape rates have been increased to a point where the above described advantages of the photon-counting detector have substantially diminished.

Because of the above described prior art, there remains a desire to improve CT imaging using photon-counting detectors without suffering from the known disadvantages such as the high cost and the low sampling rate.

BRIEF DESCRIPTION OF THE DRAWINGS

FIG. 5 is a flow chart illustrating steps or acts involved in an exemplary process of pansharpening low-resolution spectral images to generate high-resolution spectral images based upon at least one high-resolution panchromatic image according to the current invention.

FIG. 6 is a flow chart illustrating steps or acts involved in more detailed aspects of the pansharpening step in one exemplary process according to the current invention.

DETAILED DESCRIPTION OF THE PREFERRED EMBODIMENT(S)

Figure 1:
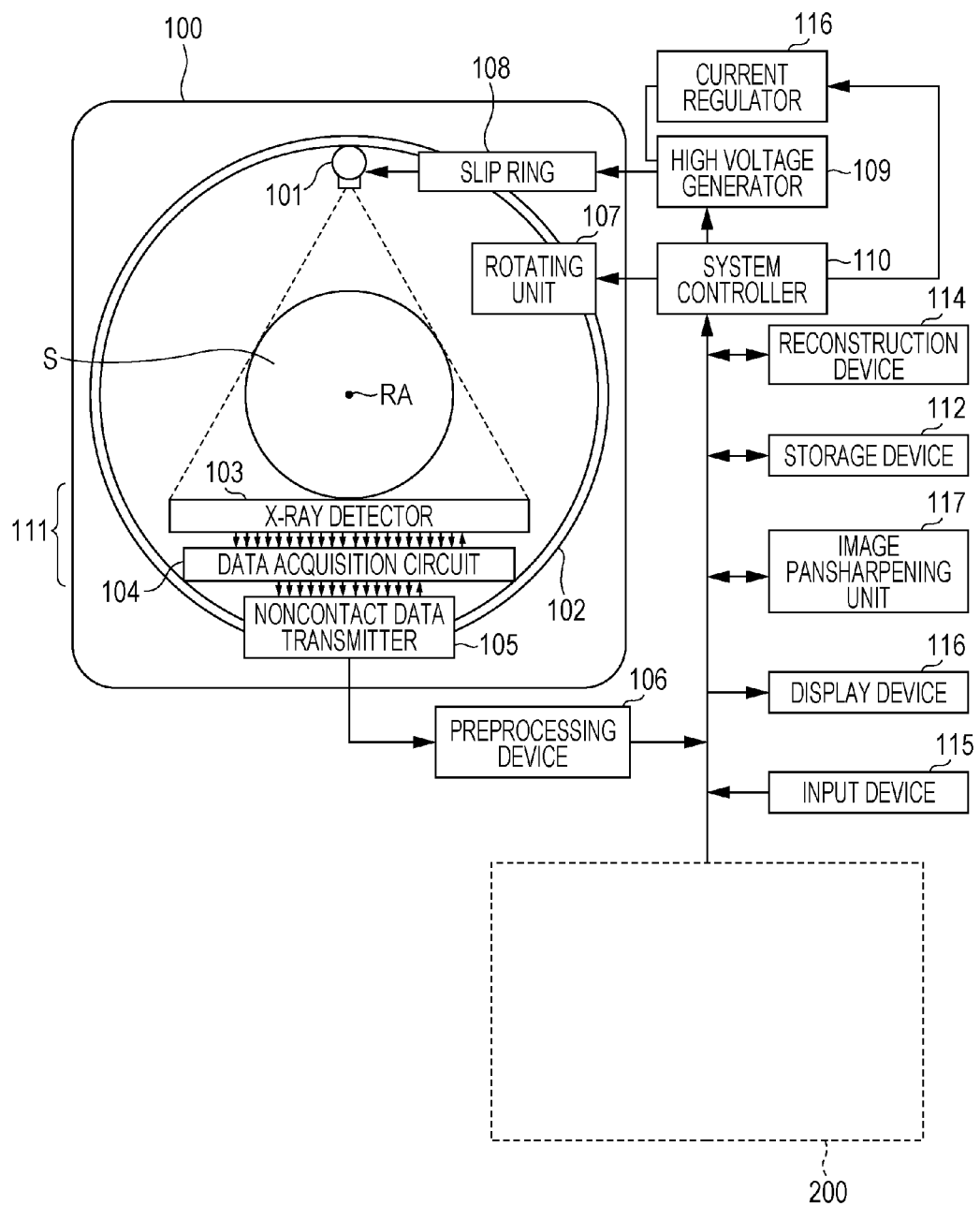
FIG. 1 is a diagram illustrating one embodiment of the multi-slice X-ray CT apparatus or scanner for pansharpening a low-resolution spectral image according to the current invention.

Referring now to the drawings, wherein like reference numerals designate corresponding structures throughout the views, and referring in particular to FIG. 1, a diagram illustrates one embodiment of the multi-slice X-ray CT apparatus or scanner for pansharpening a low-resolution spectral image according to the current invention including a gantry 100 and other devices or units. The gantry 100 is illustrated from a front view and further includes an X-ray tube 101, an annular frame 102 and a multi-row or twodimensional array type X-ray detector 103. The X-ray tube 101 and X-ray detector 103 are diametrically mounted across a subject S on the annular frame 102, which rotates around axis RA. Although a single pair of the X-ray tube 101 and X-ray detector 103 is illustrated in the diagram, the embodiment for pansharpening a low-resolution spectral image optionally includes more than a single pair of the X-ray tube 101 and X-ray detector 103. A rotating unit 107 rotates the frame 102 at a high speed such as 0.4 sec/rotation while the subject S is being moved along the axis RA into or out of the illustrated page.

The multi-slice X-ray CT apparatus further includes a high voltage generator 109 that applies a tube voltage to the X-ray tube 101 so that the X-ray tube 101 generates X ray. In one embodiment, the high voltage generator 109 is mounted on the frame 102. The X rays are emitted towards the subject S, whose cross sectional area is represented by a circle. The X-ray detector 103 is located at an opposite side from the X-ray tube 101 across the subject S for detecting the emitted X rays that have transmitted through the subject S.

Still referring to FIG. 1, the X-ray CT apparatus or scanner further includes a data acquisition device 111 for detecting the emitted X rays and processing the detected signals. In one embodiment, the X-ray detector 103 is implemented using photon counting detectors for counting photons in each of a predetermined number of energy bins. Each of the energy bins defines a predetermined range of energy in the transmitted X-ray at the detector 103. Furthermore, the X-ray detector 103 is implemented using a combination of photon-counting detectors and energy-integrating detectors. After detecting the emitted X rays at the X-ray detector 103, a data acquisition circuit 104 converts a signal output from the X-ray detector 103 for each channel into a voltage signal, amplifies it, and further converts it into a digital signal. The X-ray detector 103 and the data acquisition circuit 104 are configured to handle a predetermined total number of projections per rotation (TPPR).

In one embodiment of pansharpening spectral images according to the current invention, the X-ray detector 103 includes a combination of photon-counting detectors and energy-integrating detectors. The photon-counting detectors detect low-resolution spectral data while the energy-integrating detectors detect high-resolution panchromatic (non-spectral) data. Although one exemplary configuration of the photon-counting detectors and the energy-integrating detectors will be illustrated in another embodiment with respect to FIG. 2, the current invention as recited in the appended claims is not necessarily limited to a specific geometric configuration and includes variations.

The above described data is sent to a preprocessing device 106, which is housed in a console outside the gantry 100 through a non-contact data transmitter 105. The preprocessing device 106 performs certain corrections such as sensitivity correction on the raw data. A storage device or data storing unit 112 then stores the resultant data that is also called projection data at a stage immediately before reconstruction processing. The storage device 112 is connected to a system controller 110 through a data/control bus, together with an image reconstruction unit or device 114, a display device 116, an input device 115, and a scan plan support apparatus 200. The scan plan support apparatus 200 includes a function for supporting an imaging technician to develop a scan plan.

According to one aspect of the current invention, one embodiment of the image reconstruction device 114 reconstructs an image from the projection data that is stored in the storage device 112 based upon a predetermined reconstruction process such as a filtered backprojection (FBP) technique. In another embodiment, the reconstruction device 114 optionally reconstructs an image from the projection data based upon a filtered backprojection (FBP) technique with an additional feature of emulating a specific iteration result at a predetermined number of iterations according to a predetermined iterative reconstruction algorithm. In general, the reconstruction device 114 generates a high-resolution panchromatic (non-spectral) image from the projection data initially acquired by the energy integrating detectors as well as a low-resolution spectral image from the projection data initially acquired by the photon-counting detectors.

The reconstruction device 114 is implemented in a combination of software and hardware and is not limited to a particular implementation. In the following description of the reconstruction device 114, the term, "unit" or "device" is inclusive of hardware and or software. Furthermore, the concept of the reconstruction device 114 is applicable to other modalities including nuclear medicine and magnetic resonance imaging (MRI).

One embodiment for pansharpening spectral images also includes an image pansharpening device or unit 117 according to the current invention. The image pansharpening unit 117 receives a high-resolution panchromatic image and at least one low-resolution spectral image and pansharpens at least the one low-resolution spectral image using the high-resolution panchromatic image based upon a predetermined technique to generate a high-resolution spectral image as a pansharpened image. In general, the predetermined technique involves a pansharpening algorithm that fuses high-resolution information into a low-resolution spectral image to generate a high-resolution spectral image.

Figure 2:
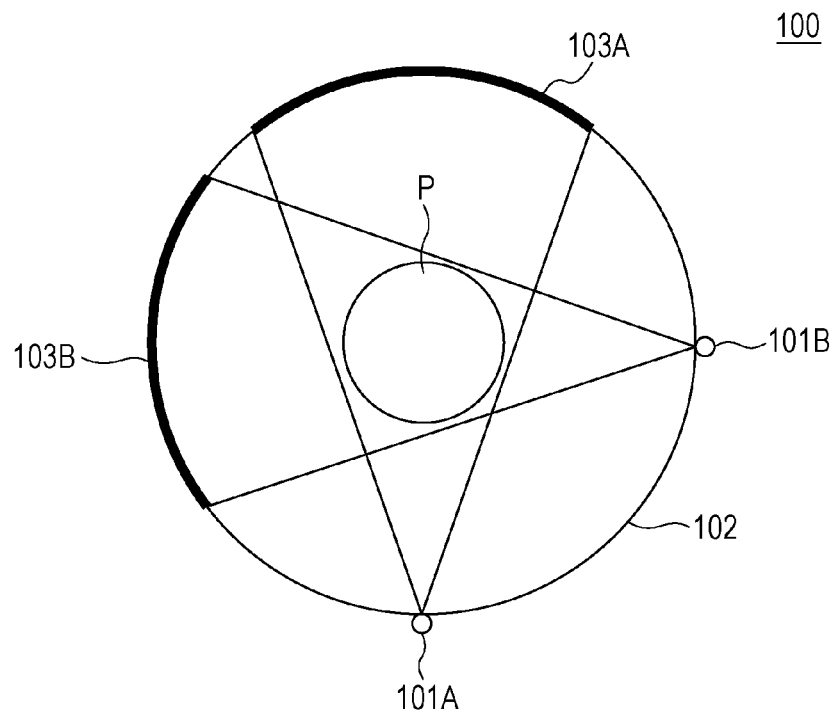
FIG. 2 is a diagram illustrating a partial diagram of a hybrid photo counting CT in one embodiment for pansharpening a low-resolution spectral image according to the current invention.

Now referring to FIG. 2, a diagram illustrates a partial diagram of a hybrid photo counting CT in one embodiment for pansharpening a low-resolution spectral image according to the current invention. The diagram illustrates the frame 102, on which two pairs of a detector and an X-ray source are fixedly mounted in a predetermined configuration. For each of the two pairs, a detector and an X-ray source are diametrically placed across a patient P. A first pair includes a first X-ray source 101A and a photon-counting detector 103A while a second pair includes a second X-ray source 101B and an energy-integrating detector 103B. The first pair and the second pair are placed at a particular angle with each other in one embodiment. Furthermore, the photon-counting detector 103A has a pixel size that is substantially larger than that of the energy-integrating detector 103B. Both the first X-ray source 101A and the second X-ray source 101B are polychromatic in one embodiment according to the current invention.

Figure 3:
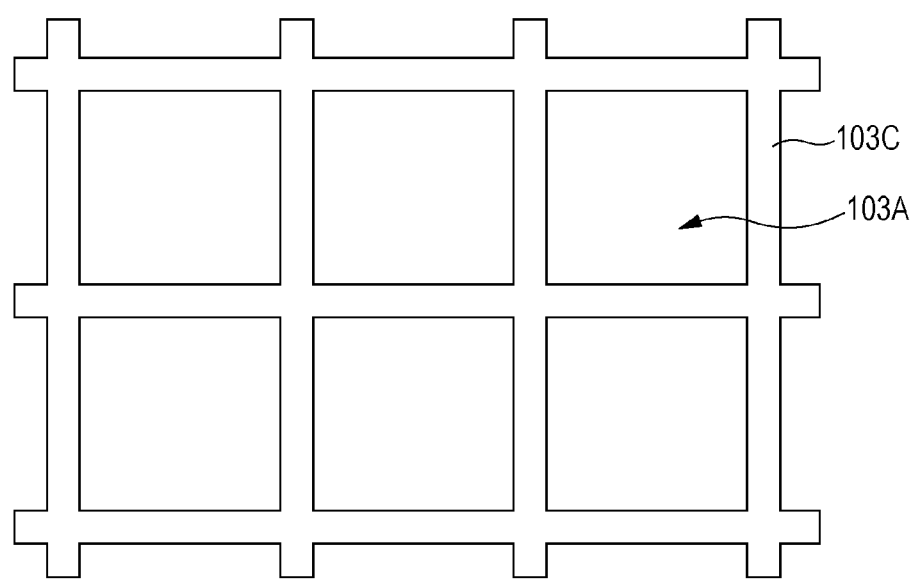
FIG. 3 is a diagram illustrating a partial top view of a 2-D photon counting detector in one embodiment according to the current invention.

FIG. 3 is a diagram illustrating a partial top view of a 2-D photon counting detector in one embodiment according to the current invention. An anti-scatter grid or collimator 103C is placed over the photon counting detector such as a CZT/CdTe sensor 103A for defining a pixel size. The pixel size of the photon-counting detector 103A of FIG. 3 is substantially larger than that of the energy-integrating detector 103B of FIG. 2. That is, the photon-counting pixel size is two to four times larger than the energy-integrating pixel size in one implementation. Furthermore, one implementation of the anti-scatter grid 103C utilizes a grid thickness of at least about 200 microns in one implementation. The minimum thickness substantially minimizes the cross-talk interference of the adjacent ones of the detector elements in the photon counting detector 103A. In general, the noise is consequently reduced in the above described implementations. On the other hand, collimation may be required to reduce flux to avoid pulse pileup in the above described implementations.

The configurations as illustrated in FIGS. 1, 2 and 3 are mere illustrations for implementing the parts of a hybrid photon-counting CT in one embodiment in acquiring data for pansharpening a low-resolution spectral image based upon a high-resolution panchromatic image according to the current invention. To practice the current invention as recited in the claims, there are not necessarily specific requirements as to how the photon-counting detectors and the energy-integrating detector are employed to acquire low-resolution spectral data and high-resolution panchromatic data. By the same token, there are not necessarily specific requirements as to how the low-resolution spectral image and the high-resolution panchromatic image are generated from the low-resolution spectral data and the high-resolution panchromatic data. Lastly, there are not necessarily specific requirements as to how much larger the photon-counting pixel size should be with respect to the energy-integrating pixel size.

Figure 4:
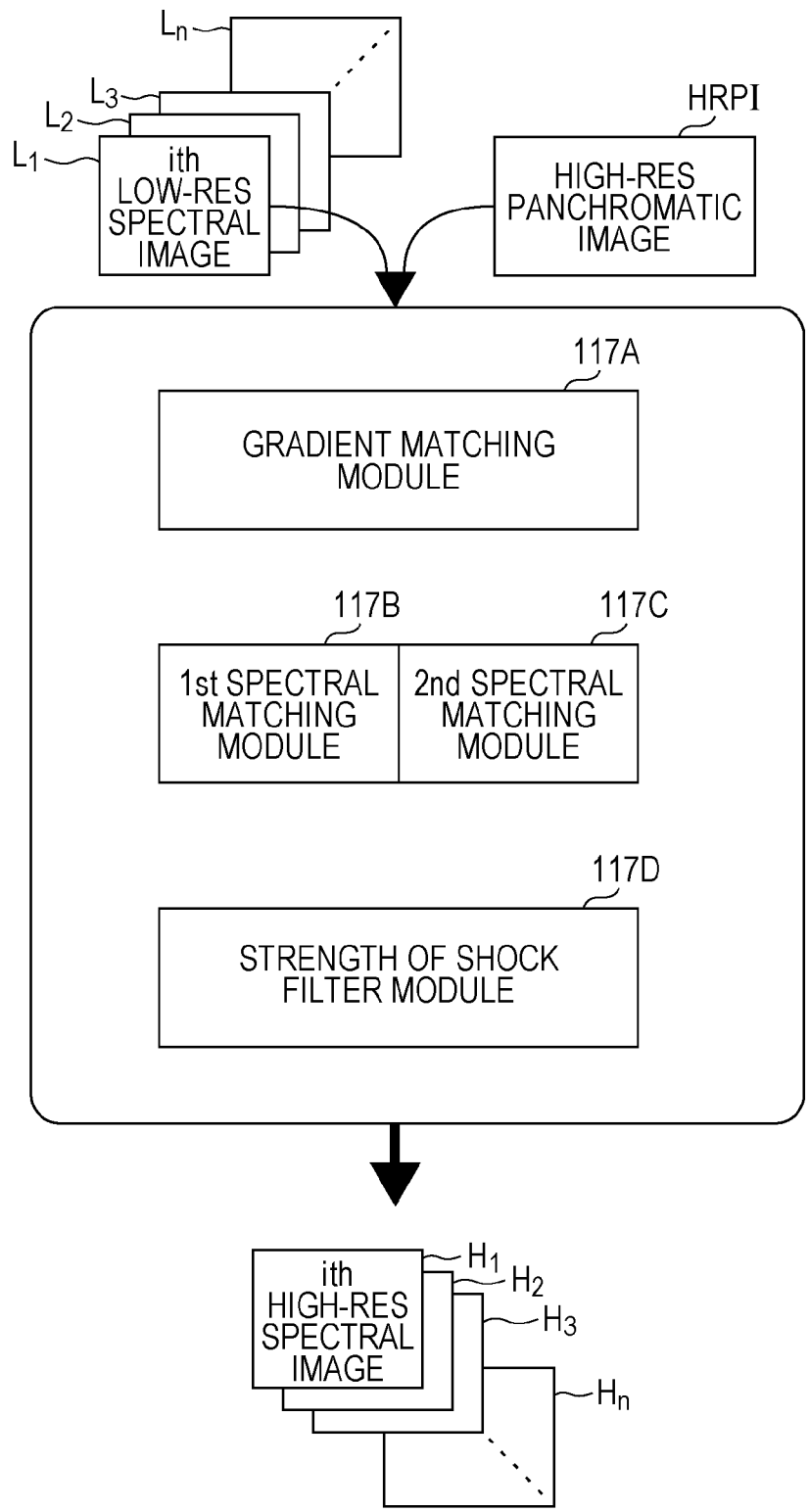
FIG. 4 is a diagram illustrating one embodiment of the image pansharpening unit according to the current invention.

Now referring to FIG. 4, a diagram illustrates one embodiment of the image pansharpening unit 117 according to the current invention. The image pansharpening unit 117 receives a predetermined number of images as inputs. In general, the image pansharpening unit 117 receives a set of low-resolution spectral images L1 through Ln, each corresponding to one of the predetermined bins of the photon-counting detectors. That is, each of the low-resolution images L1 through Ln has been reconstructed from the corresponding spectral data which was acquired at a particular bin of the photo-counting detectors. For example, if the photon-counting detector has a predetermined number of n bins, n low-resolution images L1 through Ln have been generated, and up to n low-resolution images are inputted into the image pansharpening unit 117 for being pansharpened to improve their resolution. At the same time, a single high-resolution panchromatic image HRPI is also inputted into the image pansharpening unit 117. That is, the high-resolution panchromatic image HRPI has been reconstructed from data acquired at an energy-integrating detector. The image pansharpening unit 117 outputs a set of high-resolution spectral images H1 through Hn, each corresponding to one of the predetermined bins of the photon-counting detectors.

Still referring to FIG. 4, the image pansharpening unit 117 further includes a gradient matching module 117A, a first spectral matching module 117B and a second spectral matching module 117C for ultimately outputting a set of high-resolution spectral images H1 through Hn. In addition, the image pansharpening unit 117 optionally includes a strength shock filter module 117D. In one implementation, at least some of the gradient matching module 117A, the spectral matching modules 117B, 117C and the strength shock filter module 117D are implemented as software modules. In another implementation, at least some of the gradient matching module 117A, the spectral matching modules 117B, 117C and the strength shock filter module 117D are implemented as a combination of software modules and hardware devices. To practice the current invention, additional requirements are not necessarily needed other than those as recited in the claims as to how the gradient matching module 117A, the spectral matching modules 117B, 117C and the strength shock filter module 117D are implemented.

In general, the gradient matching module 117A, the first spectral matching module 117B and the second spectral matching module 117C are implemented based upon a predetermined algorithm as described by a predetermined equation such as Equation (1) below:

$$E(f_i) = \lambda_1 E_{gradient}(f_i) + \lambda_2 E_{radiometric}(f_i) + \lambda_3 E_{correlation}(f_i) \quad (1)$$

$$= \lambda_1 \int_\Omega |\nabla f_i - \alpha(\nabla I_{pan})\nabla I_{pan}|^2 dx +$$

$$\lambda_2 \sum_{j=1}^{n} \int_\Omega (f_j^2 - M_j^2)^2 dx + \lambda_3 \sum_{j=1}^{n} \int_\Omega (f_i M_j - f_j M_i)^2 dx$$

Wherein $\alpha$ is a predetermined coefficient, $M_i$ is one of spectral images at a low resolution, $I_{pan}$ is a panchromatic image at a high resolution, and $f_i$ is a corresponding one of the pansharpened spectral images at a high resolution. That is, $f_i$ is an objective functional to be minimized for optimization. Furthermore, an omega symbol just means the area to integrate over, and the whole image is integrated in the above case. $f_j$ is summed over all j or all the images to include information from the other spectral images to substantially improve the quality of image $f_i$, the objective functional.

In one embodiment of the image pansharpening unit 117, the gradient matching module 117A performs the first term for resolution recovery as described in Equation (2), $$\lambda_1 \int_\Omega |\nabla f_i - \alpha(\nabla I_{pan})\nabla I_{pan}|^2 dx \quad (2)$$

which encourages the injection of details from the panchromatic image. A predetermined first coefficient value λ1 weighs the radiant matching term for resolution recovery and has an exemplary value of 0.1, 0.25, 0.5, 0.75 or 1.0.

By the same token, the first spectral matching module 117B performs the second term for keeping gray levels faithful to the low-resolution images as described in Equation (3), $$\lambda_2 \sum_{j=1}^{n} \int_\Omega (f_j^2 - M_j^2)^2 dx \quad (3)$$

which enforces matching of spectral characteristics with the multispectral images. The second term just matches the low resolution and the high resolution for one image at a time and then sums over all images. A predetermined second coefficient value λ2 weighs the spectral matching term for keeping gray levels faithful to low-resolution images and has an exemplary value of 0.1, 0.25, 0.5, 0.75 or 1.0.

Optionally, the second spectral matching module 117C performs the second term for keeping gray levels faithful to the low-resolution images as described in Equation (4), $$\lambda_3 \sum_{j=1}^{n} \int_\Omega (f_i M_j - f_j M_i)^2 dx \quad (4)$$

Equation (4) enforces matching of spectral characteristics with the multispectral images. The third term is called a correlation term that matches different low-resolution images. For example, the first spectral bin is matched with the second spectral bin. In any case, both the first spectral matching module 117B and the second spectral matching module 117C substantially keep gray levels faithful to the high-resolution panchromatic image. A predetermined third coefficient value λ3 weighs the spectral matching term for keeping gray levels faithful to low-resolution images and has an exemplary value of 0.1, 0.25, 0.5, 0.75 or 1.0.

In this regard, another embodiment of the image pansharpening unit 117 fails to include or deactivates the second spectral matching module 117C so that the image pansharpening unit 117 only includes the gradient matching module 117A and the first spectral matching module 117B. By deriving a first variation of the above functional, it is optionally minimized with a standard gradient descent algorithm as described in Equation (5).

$$E(f_i) = \lambda_1 \int_\Omega \|\nabla f_i - \alpha(\nabla I_{pam})\|^2 dxdy + \lambda_2 \int_\Omega (f_i - M_i)^2 dxdy \quad (5)$$

To reiterate some of the notations, $M_i$ is one of the spectral images at a low resolution, $I_{pan}$ is a panchromatic image at a high resolution, and $f_i$ is a corresponding one of the pansharpended spectral images at a high resolution. That is, $f_i$ is an objective functional to be minimized for optimization.

Yet in another embodiment, the strength shock filter module 117D optionally performs the following term for promoting sharpening of an image as described in Equation (6), $$\lambda_4 |\nabla f_i^k| \text{sign}(\Delta f_i^k) dx \quad (6)$$

The above term is called an inverse diffusion term for sharpening an image in an updating equation such as steepest descent as shown in Equation (7). A predetermined fourth coefficient value λ4 weighs the inverse diffusion term for the strength of the shock filter.

$$\frac{f_i^{k+1} - f_i^k}{\Delta t} = \quad (7)$$

$$-2\lambda_1(\text{div}(\alpha(\nabla I_{pan})\nabla I_{pan}) - \Delta f_i^k) - 4\lambda_2 \sum_{j=1}^{n} ((f_j^k)^2 - M_j^2) f_i^k -$$

$$2\lambda_3 \sum_{j=1}^{n} (f_i^k M_j - f_j^k M_i) M_j - \lambda_4 |\nabla f_i^k| \text{sign}(\Delta f_i^k),$$

The above four predetermined coefficients λ1 through λ4 are used to weigh the relative emphasis among the four competing terms of the gradient matching module 117A, the first spectral matching module 117B, the second spectral matching module 117C and the strength shock filter module 117D for ultimately outputting a set of high-resolution spectral images H1 through Hn. Other embodiments of the image pansharpening unit 117 are not limited to the above described modules and optionally include other modules. In any case, the embodiments are implemented in a variety of ways to control these modules so that some or all of the modules are optionally operated in parallel.

Now referring to FIG. 5, a flow chart illustrates steps or acts involved in an exemplary process of pansharpening low-resolution spectral images to generate high-resolution spectral images based upon at least one high-resolution panchromatic image according to the current invention. The exemplary process merely illustrates certain steps that are optionally combined into a single step or that are optionally further divided into sub-steps. To perform the current invention, the exemplary process is not necessarily limited to the illustrated steps or acts. In addition, each of the steps and acts does not necessarily correspond to a single unit or device and is optionally performed by more than a single unit or device.

Still referring to FIG. 5, low-resolution spectral images are obtained in a step S100. In one embodiment, a predetermined number of low-resolution spectral images is reconstructed from corresponding spectral bin data that is initially acquired at certain photon-counting detectors such as CdTe/CdZnTe detectors. Although the low-resolution spectral images are reconstructed from spectral data as acquired at the photon-counting detectors in the embodiment, there are no limitations as to how the low-resolution spectral images are obtained in the step S100 so long as these images are available for pansharpening.

By the same token, at least one high-resolution panchromatic image is obtained in a step S110. In one embodiment, at least one high-resolution panchromatic image is reconstructed from corresponding energy-integrating data that is initially acquired at certain energy-integrating detectors. Although the high-resolution panchromatic image is reconstructed from the integration data as acquired at the energy-integrating detector in the embodiment, there are no limitations as to how the high-resolution panchromatic image is obtained in the step S110 so long as the image is available for pansharpening. Furthermore, the chronological sequence of the steps S100 and S110 is irrelevant to the claimed invention. In this regard, the steps S100 and S110 are optionally performed in parallel in the claimed invention.

Still referring to FIG. 5, after a plurality of the low-resolution spectral images and at least the one high-resolution panchromatic image have been obtained, each of the low-resolution spectral images is pansharpened according to a predetermined technique such as one of the above algorithms based upon the high-resolution panchromatic image as well as other low-resolution spectral images in a step S120. The pansharpening step S120 is not limited to a particular algorithm and possibly includes other variations of the above described pansharpening algorithms. According to one embodiment, one exemplary algorithm is performed by a certain combination of the gradient matching module 117A, the first spectral matching module 117B, the second spectral matching module 117C and the strength shock filter module 117D as illustrated in FIG. 4 for ultimately outputting a set of high-resolution spectral images H1 through Hn. The gradient matching module 117A, the first spectral matching module 117B, the second spectral matching module 117C and the strength shock filter module 117D respectively perform the various aspects of the pansharpening step S120 as described by Equations (2), (3), (4) and (6).

Because of the above described features of the exemplary process, multiple sets of the high-resolution spectral images are optionally obtained based upon the selected pansharpening techniques. Furthermore, each of the high-resolution spectral images is optionally obtained based upon a selected pansharpening technique according to particular needs in the region of interest (ROI). In other words, the selected pansharpening technique is not necessarily identical in pansharpening the multiple low-resolution spectral images in the step S120.

As a result of the pansharpening step S120, the high-resolution spectral images are outputted in a step S130 according to the current invention. The outputting step S130 is optionally sequential as one object functional $f_i$ is minimized and the corresponding high-resolution spectral image is outputted in one exemplary process. In another exemplary process, the outputting step S130 waits till all of the high-resolution spectral images are obtained. In any case, each of the high-resolution spectral images is outputted for use at the end of outputting step 130.

After generally described with respect to the pansharpening step S120 in FIG. 5, more detailed aspects of the pansharpening step S120 are further illustrated in FIG. 6 in one exemplary process according to the current invention. In one exemplary process, the pansharpening step S120 further includes a step S200 of selecting ith bin of the spectral data, a step S210 of minimizing an object functional, a step S220 of optionally adjusting parameters or weights and a step of determining as to whether or not every low-resolution spectral image is pansharpened.

Still referring to FIG. 6, the selecting bin step S200 selects a low-resolution spectral image corresponding to the ith bin of the spectral data that has been acquired at a predetermined photon-counting detector. In one embodiment, the ith bin is sequentially selected from 1 through nth bin by incrementing an index i by one. In another embodiment, the ith bin is optionally selected by a user based certain spectral information with respect to a particular material basis. For example, the five spectral images are obtained from the spectral data as acquired by the photo-counting detectors with 5 bins.

In the minimizing step S210, the objective functional is minimized for the selected low-resolution spectral image corresponding to the ith bin of the spectral data. As described above, the pansharpening images are found by minimizing the energy functional such as Equation (5) in one embodiment. In general, the use of pansharpening technique is computationally efficient than the use of an iterative technique for improving the low-resolution spectral image. On the other hand, the use of pansharpening technique is optionally combined with the use of an iterative technique in an alternative embodiment.

In the parameter adjusting step S220, certain predetermined parameters are optionally adjusted to further improve the quality of the spectral images during the pansharpening process according to the current invention. The optional parameters include the weights such as $\lambda 1, \lambda 2, \lambda 3$ and $\lambda 4$ as well as $\alpha$ as illustrated in Equation (1). In this regard, $\alpha$ is a predetermined coefficient. The predetermined first coefficient value $\lambda 1$ weighs the gradient matching term for resolution recovery and has an exemplary value of 0.1, 0.25, 0.5, 0.75 or 1.0. The predetermined second coefficient value $\lambda 2$ weighs the spectral matching term for keeping gray levels faithful to low-resolution images and has an exemplary value of 0.1, 0.25, 0.5, 0.75 or 1.0. The predetermined third coefficient value $\lambda 3$ weighs the spectral matching term for keeping gray levels faithful to low-resolution images and has an exemplary value of 0.1, 0.25, 0.5, 0.75 or 1.0. The parameter values are often empirically adjusted based upon the user input.

Lastly, it is determined as to whether or not the pansharpening process should be terminated according to the current invention. That is, it is generally determined whether or not every one of the low-resolution spectral images of interest has been pansharpened according to a predetermined technique in the steps S200 through S210. If it is determined in the step S230 that every one of the low-resolution spectral images has been pansharpened, the exemplary pansharpening process terminates itself. On the other hand, if it is determined in the step S230 that not every one of the low-resolution spectral images has been pansharpened, the exemplary pansharpening process continues by repeating from the selecting step S200.

Figure 7A:
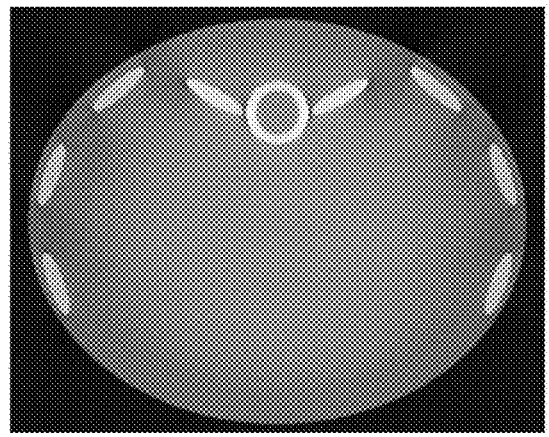
FIG. 7A is a 512×512 true image or a high-resolution panchromatic image of a predetermined phantom that has been reconstructed from non-spectral data which has been acquired at a certain energy-integrating detector of the CT system according to the current invention.
Figure 7B:
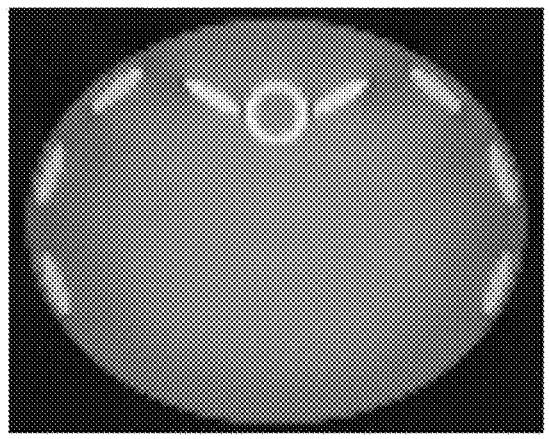
FIG. 7B is a 128×128 low-resolution spectral image of the same predetermined phantom that has been reconstructed from spectral data which has been acquired in a first bin of a certain photon-counting detector of the CT system according to the current invention.
Figure 7C:
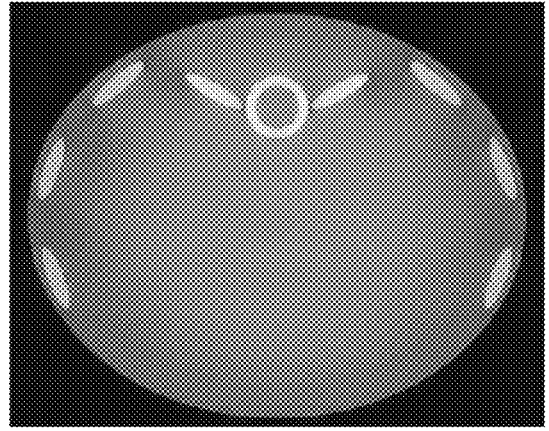
FIG. 7C is a 512×512 high-resolution pansharpened spectral image of a predetermined phantom that has been generated from the high-resolution panchromatic image of FIG. 7A and the low-resolution spectral image of FIG. 7B based upon a predetermined pansharpening technique in the CT system according to the current invention.

Now referring to FIGS. 7A, 7B and 7C, images illustrate an exemplary result of a pansharpened image according to the current invention. FIG. 7A is a 512×512 true image or a high-resolution panchromatic image of a predetermined phantom that has been reconstructed from non-spectral data which has been acquired at a certain energy-integrating detector of the CT system according to the current invention. Although a single image is illustrated in the example, a plurality of the high-resolution panchromatic images is optionally utilized according to the current invention. The high-resolution panchromatic image has been reconstructed based upon a predetermined reconstruction algorithm.

FIG. 7B is a 128×128 low-resolution spectral image of the same predetermined phantom that has been reconstructed from spectral data which has been acquired in a first bin of a certain photon-counting detector of the CT system according to the current invention. Although a single image is illustrated in the example, a plurality of the low-resolution spectral images is optionally utilized according to the current invention. The low-resolution spectral image has been reconstructed based upon a predetermined reconstruction algorithm. In this regard, the same predetermined reconstruction algorithm is used to reconstruct the high-resolution panchromatic image and the low-resolution spectral image in one embodiment. On the other hand, a different predetermined reconstruction algorithm is optionally used between the high-resolution panchromatic image and the low-resolution spectral image in another embodiment.

FIG. 7C is a 512×512 high-resolution pansharpened spectral image of the same predetermined phantom that has been generated from the high-resolution panchromatic image of FIG. 7A and the low-resolution spectral image of FIG. 7B based upon a predetermined pansharpening technique in the CT system according to the current invention. The high-resolution pansharpened spectral image has been generated based upon a predetermined pansharpening algorithm which is selected from a group of pansharpening algorithms that includes certain variations including various terms as described above in Equations (1) through (6). The spectral image as illustrated in FIG. 7C has substantially improved its resolution over the low-resolution spectral image of FIG. 7B while it maintains its spectral characteristics. In addition, a plurality of high-resolution pansharpened spectral images is optionally generated according to the current invention.

Figure 8A:
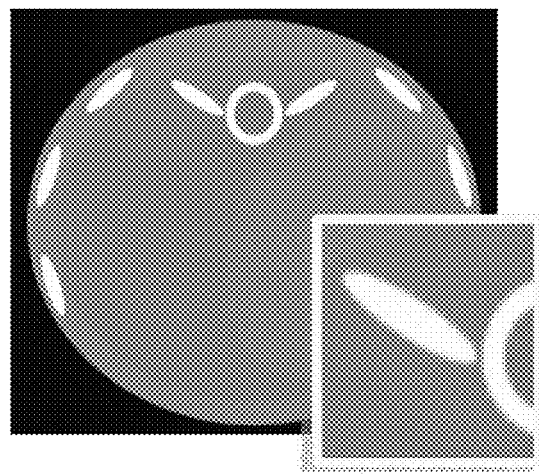
FIG. 8A is a 512×512 true image or a high-resolution panchromatic image of a predetermined phantom and a partial ROI image have been reconstructed from non-spectral data which has been acquired at a certain energy-integrating detector of the CT system according to the current invention.
Figure 8B:
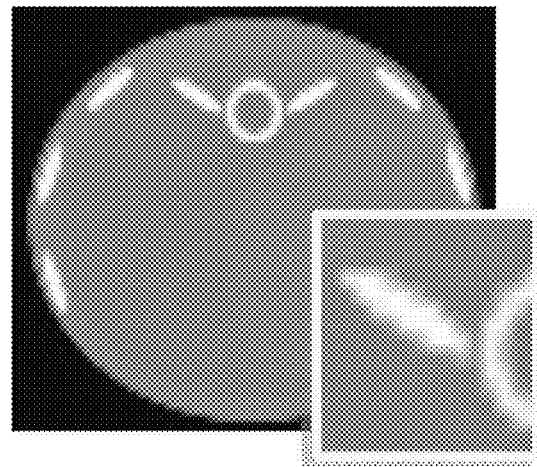
FIG. 8B is a 128×128 low-resolution spectral image and a partial ROI image of the same predetermined phantom that have been reconstructed from spectral data that has been acquired in the fourth energy bin (80-120 keV) of a certain photon-counting detector of the CT system according to the current invention.
Figure 8C:
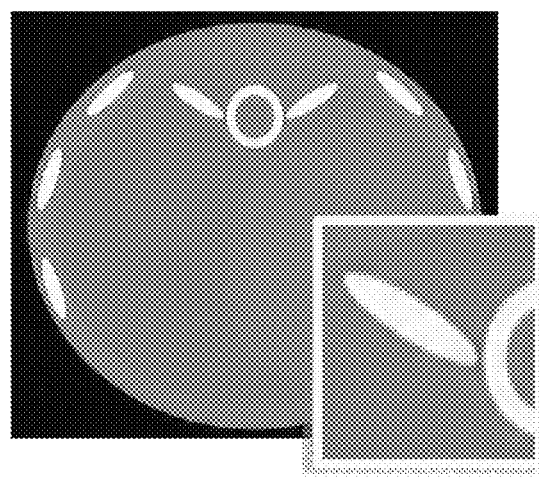
FIG. 8C is a high-resolution pansharpened spectral image and a partial ROI image that have been generated from the high-resolution panchromatic image of FIG. 8A and the low-resolution spectral image of FIG. 8B based upon a predetermined pansharpening technique in the CT system according to the current invention.

Now referring to FIGS. 8A, 8B and 8C, a region of interest (ROI) is substantially improved based upon a predetermined pansharpening technique in the CT system according to the current invention. One of the exemplary phantoms represents an axial slice through the abdomen and contains ellipses made of bone, liver, water and muscle. In general, the pan-sharpened images from each of the energy bins of the photon counting detector have substantially recovered nearly all of the resolution of the ground-truth or the high-resolution panchromatic image with some minor exceptions of spectral distortion in the high contrast objects. FIG. 8 illustrates the improvement in a particular ROI in the low-resolution image from a particular energy bin.

Still referring to FIG. 8A, a 512×512 true image or a high-resolution panchromatic image of a predetermined phantom and a partial ROI image have been reconstructed from non-spectral data which has been acquired at a certain energy-integrating detector of the CT system according to the current invention. Although a single ROI image is illustrated in the example, a plurality of ROI images is optionally utilized according tot the current invention. The high-resolution panchromatic image has been reconstructed based upon a predetermined reconstruction algorithm. In a lower right corner, a partial high-resolution panchromatic image has been selected from a predetermined ROI.

FIG. 8B is a 128×128 low-resolution spectral image and a partial ROI image of the same predetermined phantom that have been reconstructed from spectral data that has been acquired in the fourth energy bin (80-120 keV) of a certain photon-counting detector of the CT system according to the current invention. Although a single image is illustrated in the example, a plurality of the low-resolution spectral images is optionally utilized according tot the current invention. The low-resolution spectral image has been reconstructed based upon a predetermined reconstruction algorithm. In this regard, the same predetermined reconstruction algorithm is used to reconstruct the high-resolution panchromatic image and the low-resolution spectral image in one embodiment. On the other hand, a different predetermined reconstruction algorithm is optionally used between the high-resolution panchromatic image and the low-resolution spectral image in another embodiment. In a lower right corner, a partial low-resolution spectral image has been selected from the same predetermined ROI.

FIG. 8C is a high-resolution pansharpened spectral image and a partial ROI image that have been generated from the high-resolution panchromatic image of FIG. 8A and the low-resolution spectral image of FIG. 8B based upon a predetermined pansharpening technique in the CT system according to the current invention. The high-resolution pansharpened spectral image has been generated based upon a predetermined pansharpening algorithm which is selected from a group of pansharpening algorithms that includes certain variations including various terms as described above in Equations (1) through (6). The spectral image as illustrated in FIG. 8C has substantially improved its resolution over the low-resolution spectral image of FIG. 8B while it maintains its spectral characteristics. In a lower right corner, a partial high-resolution spectral ROI image has been selected from the same predetermined ROI. Alternatively, a high-resolution pansharpened spectral ROI image has been generated according to a predetermined pansharpening technique based upon the high-resolution panchromatic ROI image and the low-resolution spectral ROI image. In addition, a plurality of high-resolution pansharpened spectral ROI images is optionally generated according to the current invention.

Now referring to FIG. 9, a pair of graphs depicts how an exemplary pansharpening process according to the current invention affects material classification. Using a predetermined material classification phantom containing disks of various iodine and calcium concentrations, an exemplar pan-sharpening process fails to affect material classification tasks as depicted by the scatter plots from ROI's in the different disks. From the scatter plots, material classification is largely unaffected by the exemplary pansharpening process according to the current invention.

Figure 9A:
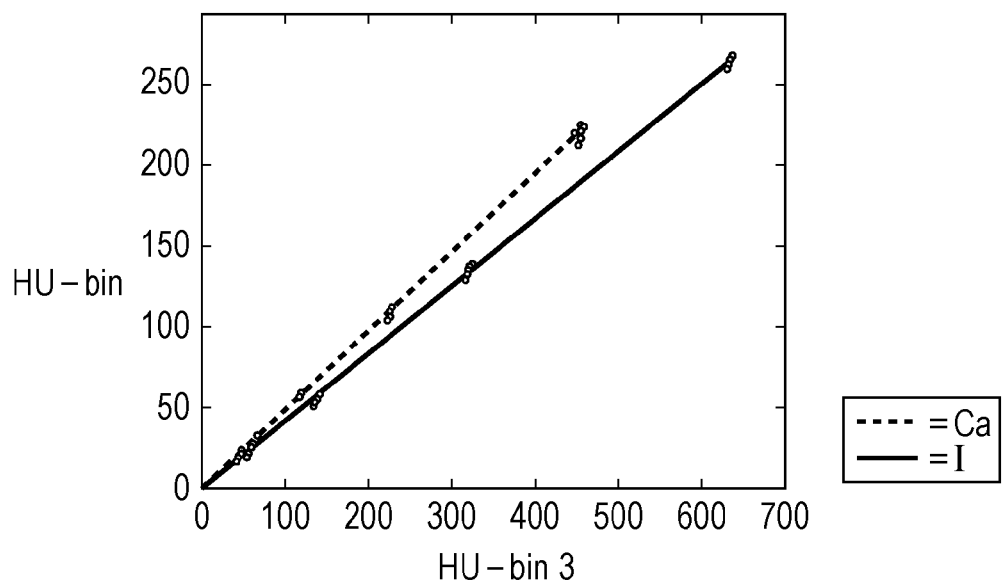
FIG. 9A is a scatter plot depicting material classification of calcium and iodine with an angler separation of 3.5 degrees in the high-resolution pansharpened spectral image.

Now referring to FIG. 9A, the scatter plot depicts material classification of calcium and iodine with an angler separation of 3.5 degrees in the high-resolution pansharpened spectral image. The x axis is a HU value in the third energy bin while the y axis is a HU value in the fourth energy bin. Furthermore, a solid line indicates iodine while a dotted line indicates calcium. Both the material classifications of calcium and iodine are substantially linear between the third and fourth bins in the high-resolution pansharpened spectral image after the exemplary pansharpening process according to the current invention.

Figure 9B:
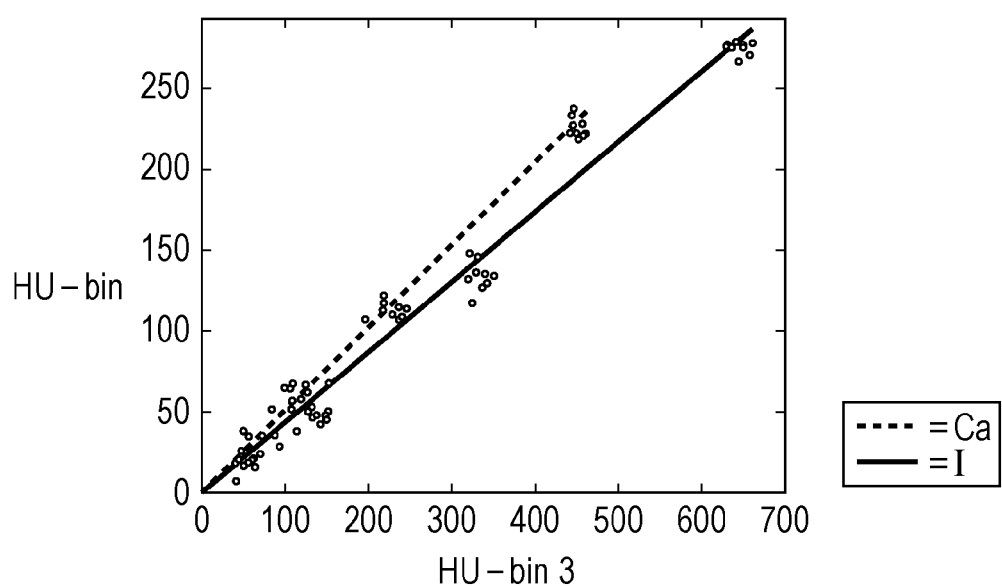
FIG. 9B is the scatter plot depicting material classification of calcium and iodine with an angler separation of 3.3 degrees in the high-resolution photon-counting image.

Now referring to FIG. 9B, the scatter plot depicts material classification of calcium and iodine with an angler separation of 3.3 degrees in the high-resolution photon-counting image. The x axis is a HU value in the third energy bin while the y axis is a HU value in the fourth energy bin. Furthermore, a solid line indicates iodine while a dotted line indicates calcium. Both the material classifications of calcium and iodine are substantially linear between the third and fourth bins in high-resolution photon-counting image before the exemplary pansharpening process according to the current invention. As a result of comparison between the two scatter plots in FIGS. 9A and 9B, material classification of calcium and iodine is largely unaffected the third and fourth bins by the exemplary pansharpening process according to the current invention.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:
1. A method of improving a spectral image, comprising;
   reconstructing a whole high-resolution panchromatic image based upon energy integration data from energy integrating detectors;
   reconstructing at least one whole low-resolution spectral image based upon spectral energy data from photon counting detectors; and
   pansharpening at least the one whole low-resolution spectral image using the whole high-resolution panchromatic image to generate a high-resolution spectral image as a pansharpened image, wherein a first flux rate of X ray entering the photon counting detectors is lower than a second flux rate of X ray entering the energy integrating detectors.

2. The method of improving a spectral image according to claim 1 further comprising an additional steps of:
   acquiring the energy integration data at the energy integrating detectors having a second detector element size;
   acquiring the spectral energy data at the photon counting detectors having a first detector element size that is larger than the second detector element size.

3. The method of improving a spectral image according to claim 2 wherein said acquiring the spectral energy data and said acquiring the energy integration data utilize two separate sources.

4. The method of improving a spectral image according to claim 1 further comprising an additional step of iteratively reconstructing an image using the high-resolution spectral image as a seed image.

5. The method of improving a spectral image according to claim 1 wherein said pansharpening uses a predetermined algorithm as described by $$E(f_i) = \lambda_1 \int_\Omega \|\nabla f_i - \alpha(\nabla I_{pan})\|^2 dxdy + \lambda_2 \int_\Omega (f_i - M_i)^2 dxdy$$

where $I_{pan}$ is the panchromatic image, $M_i$ is i'th channel of the whole low-resolution spectral image, $f_i$ is the i'th channel of the pansharpened image, E is minimizing energy functional, $\lambda_1$ is predetermined first coefficient value for weighing the gradient matching term for resolution recovery, $\lambda_2$ is predetermined second coefficient value for keeping gray level faithful, $\Omega$ just means the area to integrate over, $\nabla$ is gradient, dx is a location along a predetermined x axis, dy is a location along a predetermined y axis.

6. A system for improving a spectral image, comprising;
energy integrating detectors for acquiring energy integration data;
photon counting detectors for acquiring spectral energy data;
a data storing unit for storing the energy integration data and the spectral energy data, wherein a first flux rate of X ray entering said photon counting detectors is lower than a second flux rate of X ray entering said energy integrating detectors;
an image reconstruction unit connected to said data storing unit for reconstructing a high-resolution panchromatic image from the energy integration data and reconstructing at least one whole low-resolution spectral image from the spectral energy data; and
an image pansharpening unit connected to said image reconstruction unit for pansharpening the whole low-resolution spectral image using the whole high-resolution panchromatic image to generate at least one high-resolution spectral image.

7. The system for improving a spectral image according to claim 6 wherein said photon counting detectors have a first detector element size that is smaller than a second detector element size of said energy integrating detectors, the first detector element size being effectively combined to have a third element size that is larger than the second detector element size.

8. The system for improving a spectral image according to claim 6 wherein said photon counting detectors have a first detector element size that is larger than a second detector element size of said energy integrating detectors.

9. The system for improving a spectral image according to claim 6 further comprising a first source for said photon counting detectors and a second source for energy integration detectors.

10. The system for improving a spectral image according to claim 9 wherein said first source and said second source are located at a predetermined angle along the predetermined trajectory.

11. The system for improving a spectral image according to claim 6 wherein said image reconstruction unit iteratively reconstructs an image using the whole high-resolution spectral image as a seed image.

12. The system for improving a spectral image according to claim 6 wherein said image pansharpening unit for pansharpening according to a predetermined algorithm as described by $$E(f_i) = \lambda_1 \int_\Omega \|\nabla f_i - \alpha(\nabla I_{pan})\|^2 dxdy + \lambda_2 \int_\Omega (f_i - M_i)^2 dxdy$$

where $I_{pan}$ is the panchromatic image, $M_i$ is i'th channel of the whole low-resolution spectral image, $f_i$ is the i'th channel of the pansharpened image, E is minimizing energy functional, $\lambda_1$ is predetermined first coefficient value for weighing the gradient matching term for resolution recovery, $\lambda_2$ is predetermined second coefficient value for keeping gray level faithful, $\Omega$ just means the area to integrate over, $\nabla$ is gradient, dx is a location along a predetermined x axis, dy is a location along a predetermined y axis.

13. A system for improving a spectral image, comprising;
energy integrating detectors in a first predetermined detector size for acquiring energy integration data;
photon counting detectors in with a second predetermined detector size with thick anti-scatter grids for acquiring spectral energy data, the second predetermined detector size being substantially larger than the first predetermined detector size, wherein a first flux rate of X ray entering said photon counting detectors is lower than a second flux rate of X ray entering said energy integrating detectors;
a data storing unit for storing the energy integration data and the spectral energy data;
an image reconstruction unit connected to said data storing unit for reconstructing a whole high-resolution panchromatic image from the energy integration data and reconstructing at least one whole low-resolution spectral image from the spectral energy data; and
an image pansharpening unit connected to said image reconstruction unit for pansharpening the whole low-resolution spectral image using the whole high-resolution panchromatic image to generate at least one high-resolution spectral image.

\* \* \* \* \*